United States Patent [19]

Jarque et al.

[11] 4,028,371

[45] June 7, 1977

[54] THE COMPOUND 1,3,4-TRIMETHYL-1-(3,4,5-TRIMETHOXYBENZYL)-1,2,5,6-TETRAHYDROPYRIDINE CHLORIDE

[75] Inventors: Ricardo Granados Jarque; Juan Bosch Cartes; Jorge Cañals Cabiro, all of Barcelona; Cristobal Martinez Roldan; Fernando Rabadan Peinado, both of Madrid, all of Spain

[73] Assignee: Laboratorios Made, S.A., Spain

[22] Filed: Mar. 1, 1976

[21] Appl. No.: 662,577

Related U.S. Application Data

[62] Division of Ser. No. 569,193, April 17, 1975, abandoned.

[30] Foreign Application Priority Data

May 4, 1974 Spain .................................. 425970

[52] U.S. Cl. .......................... 260/297 R; 424/263; 424/330; 260/570.5 R
[51] Int. Cl.² ...................................... C07D 211/00
[58] Field of Search ............................... 260/297 R

[56] References Cited

UNITED STATES PATENTS 3,558,638  1/1971  Clarke et al. .................... 260/294.3

OTHER PUBLICATIONS

Fry et al., J. Org. Chem. vol. 26, pp. 2592 to 2594 (1961).
Alger et al., J. Org. Chem. vol. 27, pp. 245 to 247 (1962).
Jacobson et al., J. Org. Chem. vol. 32, pp. 1894 to 1896 (1967).
Block et al., J. Med. Chem. vol. 12, pp. 845 to 847 (1969).
Kanematsu et al., J. Med. Chem. vol. 12, pp. 405 to 408 (1969).

*Primary Examiner*—John D. Randolph
*Attorney, Agent, or Firm*—Marn & Jangarathis

[57] ABSTRACT

The compound 1,3,4-trimethyl-1-(3,4,5-trimethoxybenzyl)-1,2,5,6-tetrahydropyridine chloride and the Hoffmann degradation thereof to produce N-Methyl-N-(3,4,5-Trimethoxybenzyl) 2,3-Dimethyl-2,4-Pentadienamine is disclosed.

1 Claim, No Drawings

THE COMPOUND 1,3,4-TRIMETHYL-1-(3,4,5-TRIMETHOXYBENZYL)-1,2,5,6-TETRAHYDROPYRIDINE CHLORIDE

This is a division of application Ser. No. 569,193 filed Apr. 17, 1975, now abandoned.

The present invention relates to the production of N-methyl-N-(3,4,5-trimethoxybenzyl)-2, 3-dimethyl-2,4-pentadienamine having the general formula

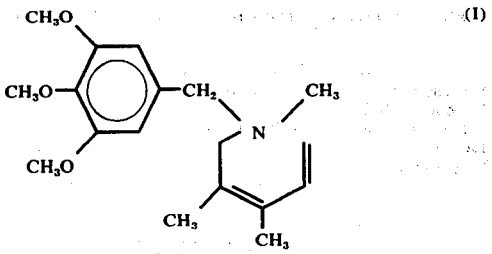

its pharmaceutically acceptable acid-addition salts, for example its hydrochloride, and an intermediate compound for preparing it: 1,3,4-trimethyl-1-(3,4,5-trimethoxybenzyl)-1,2,5,6-tetrahydropyridine chloride, having the formula

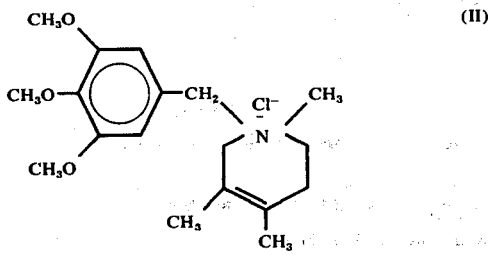

These compounds have interesting pharmaceutical properties as analgaesiacs.

The method of the invention consists in reacting, in a first syntesis stage, 3,4,5-trimethoxybenzyl having the formula

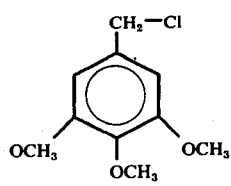

with 1,3,4-trimethyl-1,2,5,6-tetrahydropyridine having the formula

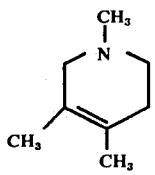

in the anhydrous solvent kept at reflux, for example acetone, which results in the production of the above-mentioned compound II when the reaction mixture is cooled.

In a second synthesis stage, the ammonium salt of formula II thus obtained is subjected to a Hoffmann degradation reaction by prolonged boiling with an aqueous solution of an alkaline metal hydroxide, for example potassium hydroxide. Extraction with ether and subsequent treatment with ether and a hydracid acid results in the halohydrate of the corresponding compound having the formula I.

The following Examples are given merely by way of illustration and the scope of the invention is in no way limited thereby.

EXAMPLE 1

Production of 1,3,4-trimethyl-1-(3,4,5-trimethoxybenzyl)-1,2,5,6-tetrahydropyridine chloride (II).

55 g of 3,4,5-trimethoxybenzyl dissolved in 200 ml of anhydrous acetone were added rapidly and while being stirred to a solution of 30 g of 1,3,4-trimethyl-1,2,5,6-tetrahydropyridine in 150 ml of anhydrous acetone. The mixture was heated for 5 hours to reflux. The mixture was allowed to cool and stirring was continued for 2 hours while the mixture was maintained at a low temperature. Finally, it was left in the cooling apparatus. The precipitate obtained was washed with acetone-ether (1:1), giving 79 g of II. Yield = 92%. An analytical sample crystallized in absolute acetone-alcohol had a boiling point of 149°– 152° C. Analysis: $C_{18}H_{28}NO_3CL.H_2O$. Calculated: C = 60.08, H = 8.40, N = 3,89. Actual: C = 59.90, H = 8.38, N = 3.85.

EXAMPLE 2

Production of N-methyl-N-(3,4,5-trimethoxybenzyl)-2,3,-dimethyl-2,4-pentadienamine (I), and its hydrochloride.

16.2 g of 1,3,4-trimethyl-1-(3,4,5-trimethoxybenzyl)-1,2,5,6-tetrahydropyridine chloride (II), 25.2 g of potassium hydroxide and 145 ml of water were kept at reflux for 33 hours, the separation of an organic layer being observed. Thereafter extraction with ether and drying with anhydrous sodium sulphate were carried out. An ethereal solution of dry hydrochloric acid was acued drop by drop until an acid pH was reached, and 9 g of the hydrochloride of the compound of formula I were precipitated. Melting point = 202° – 204° C.

While maintaining the aqueous layer etheral X during a further 45 hours, treatment similar to that described in the previous paragraph was continued and a further 2.1 g of hydrochloride were obtained, thus giving a total yield of 72%. Analysis: $C_{18}H_{28}NO_3Cl$. Calculated: C = 63.24, H = 8.25, N = 4.09. Actual: C = 63.09, H = 8.27, N = 4.12.

PROPERTIES OF THE PRODUCTS IN ACCORDANCE WITH THE INVENTION

Products

I - N-methyl-N-(3,4,5-trimethoxybenzyl)-2,3-dimethyl-2,4-pentadienamine.

II - 1,3,4-trimethyl-1-(3,4,5-trimethoxybenzyl)-1,2,5,6-tetrahydropyridine chloride.

These products have analgesic properties; studies were carried out with dextropropoxiphene as a reference analgesiac.

A - ACUTE TOXICITY

The acute toxicity studies were carried out on I.C.R. Swiss rats of both sexes and weighing 30±2, g; the products were administered intraperitoneally (i.p.).

The acute toxicity calculations were carried out by the Litchfield Wilcoxon method.

TABLE A

| Products | Lethal dose 50 (DL$_{50}$) |
|---|---|
| I | 165 mg/kg |
| II | 77 mg/kg |
| Dextropropoxiphene | 140 mg/kg |

B - ANALGESIC ACTIVITY

The analgesics effect was studied in I.C.R. Swiss albino rats, using the acetic acid writhing technique. Batches of 10 rats were treated.

The analgaesiacs were injected i.p. and after 30 minutes 0.25 ml of 1% acetic acid were injected i.p. A control batch which received only acetic acid was used. The number of writhes in each rat during the 20 minutes following the administration of acetic acid were counted.

TABLE B

| Treatment | Dose | No. of writhes (x ± S.E.M.)* | P |
|---|---|---|---|
| I | 20 mg/kg | 541 ± 4.65 | p < 0.001 |
| II | 20 mg/kg | 53.6 ± 4.7 | p < 0.001 |
| Dextropropoxiphene | 25 mg/kg | 22.8 ± 4.74 | p < 0.001 |
| Control | — | 112.2 ± 4.2 | — |

* Mean value ± standard error of average.

As can be seen from Table B, products I and II have analgesic activity.

Listed below are examples of pharmaceutical compositions containing as active ingredients the following products, combined with carriers and pharmaceutical excipients. I - N-methyl-N-(3,4,5-trimethoxybenzyl)-2,3-dimethyl-2,4-pentadienamine and its hydrochloride. II - 1,3,4-trimethyl-1-(3,4,5-trimethoxybenzyl)-1,2,5,6-tetrahydropyridine chloride.

The oral dose of product I is 2.23 mg per kg of weight and per day. An individual weighing 70 kg will be administered 150 mg daily, spread over three doses of 50 mg.

The injectable dose of compound I is 1.5 mg per kg of weight and per day. An individual weighing 70 kg will be administered 105 mg daily, spread over three injections of 35 mg each.

The oral dose of product II is similar to the preceding one.

EXAMPLE 1

Hard gelatine capsules. Composition per capsule:

| | |
|---|---|
| N-methyl-N-(3,4,5-trimethoxybenzyl)-2,3-dimethyl-2,4-Pentadienamine or its hydrochloride | 50 mg |
| Lactose | 100 mg |
| Magnesium stearate | 2.5 mg |

EXAMPLE 2

Injectable solution. Composition per ampoule:

| | |
|---|---|
| N-methyl-N-(3,4,5-trimethoxybenzyl)-2,3-dimethyl-2,4-pentadienamine hydrochloride | 35 mg |
| Sodium chloride | 27 mg |
| Sodium metabisulphite | 3 mg |
| Water for injectables | 3 ml |

EXAMPLE 3

Hard gelatine capsules. Composition per capsule:

| | |
|---|---|
| 1,3,4-trimethyl-1-(3,4,5-trimethoxybenzyl) 1,2,5,6-tetrahydropyridine chloride | 50 mg |
| Lactose | 100 mg |
| Magnesium stearate | 2.5 mg |

We claim:
1. The compound 1,3,4-trimethyl-1-(3,4,5-trimethoxybenzyl)-1,2,5,6-tetrahydropyridine chloride.

* * * * *